United States Patent [19]
Ishiguro et al.

[11] 3,988,327
[45] Oct. 26, 1976

[54] 7-(α-SULFOACYLAMIDO)CEPHALOSPORANIC ACIDS

[75] Inventors: Toshihiro Ishiguro, Osaka; Takeshi Fugono, Hyogo; Hiroaki Nomura, Osaka, all of Japan

[73] Assignee: Takeda Chemical Industries, Ltd., Japan

[22] Filed: Feb. 5, 1975

[21] Appl. No.: 547,169

Related U.S. Application Data

[63] Continuation of Ser. No. 113,935, Feb. 9, 1971, abandoned.

[30] Foreign Application Priority Data

Feb. 11, 1970 Japan.............................. 45-11620

[52] U.S. Cl............................. 260/243 C; 424/246
[51] Int. Cl.$^2$............... C07D 501/32; C07D 501/28
[58] Field of Search............................... 260/243 C

[56] References Cited
UNITED STATES PATENTS

| | | | |
|---|---|---|---|
| 3,338,897 | 8/1967 | Takano et al. ................ | 260/243 C |
| 3,382,238 | 5/1968 | Dolfini et al. .................. | 260/239.1 |
| 3,575,969 | 4/1971 | Morin et al. .................... | 260/243 C |
| 3,579,506 | 5/1971 | Lemieux et al. ................ | 260/243 C |
| 3,651,050 | 3/1972 | Nakanishi ...................... | 260/243 C |
| 3,660,379 | 5/1972 | Morimoto et al. .............. | 260/243 C |
| 3,669,980 | 6/1972 | Bogash et al. .................. | 260/243 C |

FOREIGN PATENTS OR APPLICATIONS 1,310,642    3/1973    United Kingdom

*Primary Examiner*—Nicholas S. Rizzo
*Assistant Examiner*—Diana G. Rivers
*Attorney, Agent, or Firm*—Craig & Antonelli

[57] ABSTRACT

Novel cephalosporanic acid derivatives which are active against both Gram positive and Gram negative pathogenic bacteria, particularly Pseudomonas, and which have an α-sulfoacylamino group at 7-position. A few examples of the compounds are 7-(α-sulfophenylacetamido)-cephalosporanic acid, 7-(α-sulfopropionamido)-cephalosporanic acid, 7-(α-sulfocapronamido)-cephalosporanic acid. They are prepared by condensing 7-aminocephalosporanic acid or salts thereof with α-sulfocarboxylic acid or functional derivatives thereof in the presence of a solvent at −2° − 10° C.

9 Claims, No Drawings

7-(α-SULFOACYLAMIDO)CEPHALOSPORANIC ACIDS

This is a continuation of application Ser. No. 113,935 filed Feb. 9, 1971, now abandoned.

This invention relates to novel cephalosporanic acid derivatives which are active against both Gram positive and Gram negative pathogenic bacteria and the preparation thereof. More particularly, it concerns 7-(α-sulfoacylamido)cephalosporanic acids and preparation thereof.

There are many cephalosporanic acid derivatives which are useful for Gram positive and/or negative microorganisms.

The present compounds are represented by the following formula:

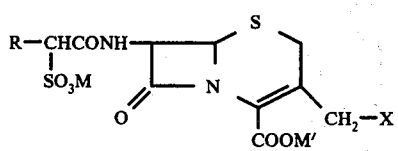

wherein
R is hydrogen atom, alkyl groups having 1–6 carbon atoms or phenyl;
M and M' may be the same with or different from each other, and each of them stands for hydrogen atom, alkali metals, alkaline earth metals or organic amines; and
X is —OCOCH$_3$ or

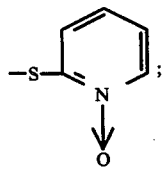

The present compounds are novel with respect to the fact that they have an α-sulfoacrylamino group at the 7-position. Typical compounds are
1. R = phenyl, M = M' = Na, X = —OCOCH$_3$
2. R = H, M = M' = Na, X = —OCOCH$_3$
3. R = CH$_3$—, M = M' = Na, X = —OCOCH$_3$
4. R = CH$_3$(CH$_2$)$_3$—, M = M' = Na, X = —OCOCH$_3$, and
5. R = phenyl, M = M' = Na,

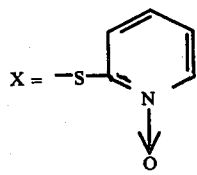

R may be ethyl, n-propyl, iso-propyl, iso-butyl, n-hexyl, cyclohexyl or the like. M and M' may be potassium, calcium, mangesium, or other non-toxic alkali or alkaline earth metals. In addition, M and M' may be such non-toxic organic amines as triethylamine, procaine, dibenzylamine, N-benzyl-β-phenethyl amine, 1-ephenamine, N,N'-bisdehydroabiethylethylenediamine, and the like. Other amines may be used as long as they have been used for salt forming with benzylpenicillin.

The present compounds have both sulfo and carboxyl groups, and may be either acid or neutral salt depending on the acidity of the above acid groups. There are one or two asymmetrical carbons in the molecule. The compounds of this invention can exist in two optically active forms (the D- and L-diastereoisomers), when α-sulfocarboxylic acids (to which the α-carbon atom is assymmetric) are used as starting materials.

The compounds are active against *Pseudomonas aeruginosa*, *Escherichia coli*, *Proteus vulgaris*, *Proteus morganii*, *Proteus mirabillis*, *Klebsiella pneumoniae*, *Staphylococcus aureus*, *Bacillus subtilis*, *Sarcina lutea* and the like. The compounds can be applied by oral administration, subcutaneous injection, or intravenous injection. Doses are from about 5 to 500 mg/kg/day, preferably about 10–200 mg/kg/day, 2–4 times applications a day, against, for example, pseudomonas infection.

The present compounds are produced by the condensation reaction of 7-cephalosporanic acid, salts or readily decomposable esters thereof with α-sulfocarboxylic acid or functional derivatives thereof.

The α-sulfocarboxylic acid, one of the starting materials, has the following formula:

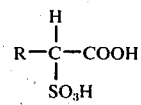

wherein R is the same as defined above.

Alpha-sulfophenyl acetic acid, α-sulfopropionic acid, α-sulfoacetic acid and others are commercially available and are prepared by sulfonating the corresponding carboxylic acids by sulfuric anhydride. The sulfo group may be protected, if desired, in the form of sulfonamide or sulfonate in the condensation step with 7-aminocephalosporanic acid.

Functional derivatives of the α-sulfocarboxylic acid are carboxylic acid halide such as chloride or bromide, mixed anhydride such as lower alkyloxy or aralkyloxycarbonic anhydride, α-toluenesulfonic anhydride, azide or activated ester such as with p-nitrophenol, 2,4-dinitrophenol or pentachlorophenol or carboazide. These derivatives can be obtained from the α-sulfocarboxylic acid by any of the conventional processes. For instance, acid halide is produced by treating the α-sulfocarboxlic acid with a halogenating agent such as, for example, thionylchloride, phosphor oxychloride or phosphor oxybromide.

Salts of 7-aminocephalosporanic acid are those at the amino group such as hydrochloride, sulfate, acetate or the like, or those at the carboxylic acid group such as sodium, potassium, triethylamine salts or the like.

Readily decomposable esters of 7-amino cephalo sporanic acid are represented by the general formula:

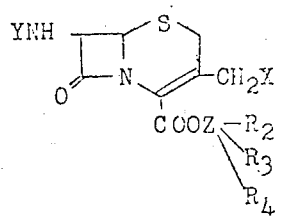

wherein X is —OCOCH$_3$

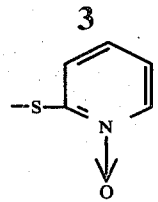

Z is silicon or tin atom;

$R_2$, $R_3$, and $R_4$ are the same or different hydrocarbon groups; and one of them may be halogen atom, and furthermore, in such case, they may combine with active hydrogen atom to form a polymer;

Y is hydrogen atom or $-ZR_2R_3R_4$.

These esters can be obtained by any conventional methods from 7-aminocephalosporanic acid. For instance, the compound, where Y is hydrogen atom, Z is tin atom, and $R_2 - R_4$ all are n-butyl group, is prepared by boiling a mixture of 7-aminocephalosporanic acid and 0.5 mol equivalent of bis(tributyltin) oxide in dry benzene for a short time.

In the present process, the amino group of the 7-aminocephalosporanic acid is condensed with the carboxylic group of the α-sulfocarboxylic acid. Such procedures are familiar with those skilled in the art.

Preferable ones are:

1. 7-aminocephalosporanic acid or salts thereof are condensed with α-sulfocarboxylic acid in the presence of a dehydrating agent. The dehydrating agent is, for example, N,N'-dicyclohexyl carbodiimide, N,N'-diisopropylcrbodiimide or N,N'-carbonyltriazole;
2. the functional derivatives of α-sulfocarboxylic acid are condensed with 7-aminocephalosporanic acid or salts thereof; and
3. the readily decomposable esters of 7-aminocephlosporanic acid are condensed with the functional derivatives of α-sulfocarboxylic acid.

The present condensation may be carried out in the presence of solvents. The solvents are water, dioxane, acetone, dimethylformamide, tetrahydrofuran, dichloromethane, chloroform, ethylene dichloride, toluene, benzene or a mixture of any of them. In the procedures 1 and 3 above, water is not desirable. In the procedures 2 and 3 above, the presence of bases is preferable. The bases are organic bases such as, for example, triethylamine, tributylamine, dimethylaniline, pyridine, picoline, quinoline. Alternatively, the bases are inorganic bases such as sodium carbonate, potassium carbonate, sodium bicarbonate, potassium bicarbonate, sodium hydroxide, potassium hydroxide, calcium hydroxide or the like.

The condensation is effected at a temperature of from −5° to 40° C., preferably −2° to 10° C. The upper limit is 50° C., because the product of cephalospranic acid derivatives are easily decomposed.

In the procedure 3 above, the product produced by the reaction is treated with water or a lower aliphatic alcohol to decompose and take off the ester group.

After the condensation is completed, the product can be purified by any of conventional means. Such means are solvent extract, concentration, chromatography, crystallization, recrystallization or the like. Thus the product can be obtained in the form of free bases or salts. The salts can be converted, if desired, into other nontoxic salts by any of conventional procedures.

The present invention will now be explained in further detail by referring to the following examples.

EXAMPLE 1

Preparation of 7-(α-sulfophenylacetamido)-cephalosporanic acid

Into a flask equipped with a stirrer were transferred 2.5 ml of 1 N-NaOH solution and 5 ml of water. The mixture was cooled to 0° − 5° C. in an ice water bath and, under the mechanical stirring, 680 mg of 7-aminocephalosporanic acid was added thereto. Then the solution which had been prepared separately by dissolving 585 mg of α-sulfophenylacetyl chloride in 7 ml of diethylether was added dropwise into the mixture over 15 minutes. The mixture was stirred for 15 minutes, and then a water layer was separated from the reaction mixture and the pH of said layer was adjusted to 1.5 with 1N-HCl. Subsequently, the layer was extracted twice with 15 ml each of n-butanol, the extract was washed twice with 5 ml each of water and thereafter further extracted with a saturated aqueous NaHCO₃ solution. The extract was adjusted to pH 6.5. After being purified by chromatography packed with polystyrene powder, the fractions of the eluate containing the objective substance was lyophilized to yield white powder in the form of sodium salt. The product was dried and analyzed to give the following results:

Yield: 385 mg

IR $\nu_{max}^{KBr}$ (cm$^{-1}$): 1755(lactam, acetate), 1612(—COO—), 1680(—CONH—), 1225(—SO₂—), 1046(—SO₃Na)

NMR(D₂O) ppm: 2.09(3H, singlet), 3.42(2H quartet $J_1$=18.0 c/s, $J_2$=18.0 c/s), Ca 4.75(2H), 5.09(1H, singlet), 5.10(1H, doublet, J=4.5 c/s), 5.70(1H, α, J=4.5 c/s), 7.52(5H, multiplet)

UV $\lambda_{max}^{H_2O}$: 259 mμ(7.1 × 10³)

EXAMPLE 2

Preparation of 7-(α-sulfophenylacetamido)-cephalosporanic acid 3.78 Grams of 7-aminocephalospranic acid was suspended in 30 ml of chloroform and 2.3 g of hexamethyldisilazane was added thereto. The mixture was heated at 65° C. for 1.5 hours in a hot water bath. The transparent solution obtained was subjected to distillation under reduced pressure at 40° C. The residual substance was redissolved in 50 ml of chloroform, and 1.94 g of triethylamine was added thereto. Then, this solution was cooled, and 30 ml of a chloroform solution containing 4.3 g of α-sulfophenylacetic acid chloride was added thereto dropwise. The mixture was stirred at 15° C. for 15 minutes. After the reaction was over, the reaction mixture was concentrated at room temperature under reduced pressure. Thereafter, the product was dissolved in 50 ml of water. The aqueous solution was adjusted to pH 1.5 and extracted twice with 35 ml each of n-butanol. The butanol layer was washed with a small portion of water and thereafter extracted again with an aqueous sodium hydrogencarbonate solution. After the pH of the solution was adjusted to 6, the objective substance was crystallized out of the solution and dried. 4.3 Grams of the sodium salt of the objective compound was obtained. The result of infra-red absorption spectrum analysis was the same as in Example 1.

EXAMPLE 3

Preparation of 7-(α-sulfoacetamido)-cephalosporanic acid

After 0.212 g of 7-aminocephalosporanic acid was suspended in 7 ml of water, 0.78 ml of 1N-NaOH and 0.153 g of sodium hydrogencarbonate was added thereto. The mixture was stirred thoroughly and cooled on an ice-water bath. Subsequently, 3 ml of chloroform containing 0.142 g of α-sulfophenylacetic acid chloride was added dropwise thereto. After the addition was over, the reaction was continued with stirring for 20 minutes under cooling. After the reaction mixture was adjusted to pH 2, it was extracted with 15 ml butanol. The extraction was repeated twice. The butanol extracts were combined and then washed with a small portion of water. To the so-treated butanol solution was added gently a dilute aqueous sodium hydroxide solution maintaining its pH at 6, whereby the objective compound was extracted into the aqueous layer. The aqueous layer was washed with ether and thereafter freeze-dried. Yield: 0.15 g The IR spectra of the compound obtained were as follows:
IR analysis $\nu_{max}^{KBr}$ (cm$^{-1}$): 3420(OH), 2950 – 3100(CH), 1760(broad C=O), 1670(sharp —CONH—), 1610(broad —COO—), 1408-1393 (broad), 1230,1050(—SO$_3$—)

EXAMPLE 4

Preparation of 7-(α-sulfopropionamido)-cephalosporanic acid 0.272 Grams of 7-aminocephalosporanic acid-(1.0 × 10$^{-3}$M) was dissolved in an aqueous sodium hydroxide solution containing 1.0 × 10$^{-3}$ mole of NaOH, and then 0.235 g(2.8 × 10$^{-3}$ M) of sodium hydrogencarbonate was added thereto. The mixture was cooled to 0° – 2° C. and 2 ml ether solution containing 0.2 g of α-sulfopropionyl chloride (1.16 × 10$^{-3}$M) was added thereto. The reaction was continued at 0° – 2° C. for 15 minutes under stirring. After the reaction was over, the pH was adjusted to 1.5 and first washed with ether and subsequently extracted twice with 10 ml of n-butanol. The extract was extracted again with an aqueous sodium hydrogencarbonate solution. After the aqueous layer was adjusted to pH 6.0, it was subjected to freeze drying. 0.2 Grams of colorless crystalline powder of the objective compound was obtained. The infra-red absorption spectrum of the compound by KBr method showed maximum peaks at the following frequencies: 3400(OH), 2950(CH), 1760(lactam), 1860(CONH), 1620(—COONa), 1410, 1230, 1045(—SO$_3$Na).

EXAMPLE 5

Preparation of 7-(α-sulfocapronamido)-cephalosporanic acid 0.2 Grams of 7-aminocephalosporanic acid (7.35 × 10$^{-3}$M) was dissolved in a mixed solvent containing 0.75 ml 1N-NaOH and 7.5 ml water, and then 0.17 g of sodium hydrogencarbonate was added thereto. The mixture was cooled to 0° – 3° C. and 2 ml ether solution containing 0.15 g (7.65 × 10$^{-4}$M) of α-sulfo-n-caproyl chloride was added thereinto. After the reaction was continued at 0° – 3° C. for 15 minutes, the reaction mixture was subjected to the same treatment as described in Example 4. Yield of the compound obtained was 0.25 g. The crude crystal was purified by means of column-chromatography using granular polystyrene (100 – 400 mesh) as fillers and water as a developer to obtain 0.1 g of pure crystal. The result of IR analysis was as follows:

IR $\nu_{max}^{KBr}$ (cm$^{-1}$): 3450(OH, broad), 2950(CH), 1760(lactam), 1675(—CONH—), 1605(—COO—), 1530, 1410, 1380, 1225(—SO$_2$—), 1180(sharp), 1043(—SO$_3$Na), 952,815,791,755,725.

EXAMPLE 6

Preparation of 7-(α-sulfophenylacetamido)-3-(2-(1-oxidopyridyl)thiomethyl)-Δ$^3$-cephem-4-carboxylic acid:

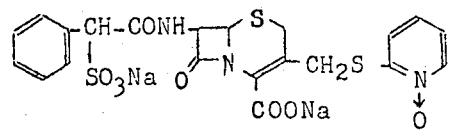

0.217 Grams of 7-(α-sulfophenylacetamido)cephalosporanic acid and 0.164 g of 2-mercaptopyridineoxide were dissolved in 15 ml water, and the pH of the liquid was adjusted to 6.4. The mixture was heated at 40° C. for 18 hours. After the reaction was over, the reaction product was subjected to freeze drying to obtain 0.350 g of powder. The objective product was separated therefrom by means of column-chromatography using cellulose powder as fillers and a mixed solvent of n-propanol, water and trichloroacetic acid (75 : 24 : 1) was a developer. The fractionate was then subjected to distillation under reduced pressure and washing with hexane. Insoluble product was combined and dissolved in water. After pH of the aqueous solution was adjusted to 6.4, the purified objective compound was lyophilized. Yield of the compound obtained was 0.080 g. The result of IR spectra was as follows: IR $\nu_{max}^{KBr}$ (cm$^{-1}$): 3450(OH), 1765(lactam), 1680(—CONH—), 1615(—COO—), 1480, 1360, 1215, 1050(—SO$_3$—), 840, 750, 705,

We claim:
1. A compound represented by the following formula:

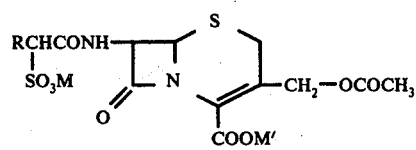

wherein
R is a hydrogen atom, alkyl having 1–6 carbon atoms or phenyl; M and M' may be the same as or different from each other, and are each a hydrogen atom, a non-toxic alkali metal, a non-toxic alkaline earth metal or a pharmaceutically acceptable non-toxic amine.

2. The compound according to claim 1, wherein M and M' are the same or different and are selected from the group consisting of hydrogen, potassium, calcium, magnesium, triethylamine, procaine, dibenzylamine, N-benzylamine, N-benzyl-β-phenethylamine, 1- ephenamine, and N,N'-bisdehydroabiethylethylenediamine.

3. The compound according to claim 1, wherein R is hydrogen.

4. The compound according to claim 1, wherein R is alkyl.

5. The compound according to claim 1 wherein R is phenyl, M and M' are each sodium.

6. The compound according to claim 1 wherein R is hydrogen, M and M' are each sodium.

7. The compound according to claim 1 wherein R is $CH_3-$, M and M' are each sodium.

8. The compound according to claim 1 wherein R is $CH_3(CH_2)_3-$, M and M' are each sodium.

9. The compound according to claim 1, wherein R is phenyl.

* * * * *